United States Patent
Leung et al.

(10) Patent No.: US 7,609,815 B2
(45) Date of Patent: Oct. 27, 2009

(54) HIGH BRIGHTNESS—MULTIPLE BEAMLETS SOURCE FOR PATTERNED X-RAY PRODUCTION

(75) Inventors: Ka-Ngo Leung, Hercules, CA (US); Qing Ji, Albany, CA (US); William A. Barletta, Oakland, CA (US); Ximan Jiang, El Cerrito, CA (US); Lili Ji, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 175 days.

(21) Appl. No.: 11/757,137

(22) Filed: Jun. 1, 2007

(65) Prior Publication Data

US 2008/0049888 A1    Feb. 28, 2008

Related U.S. Application Data

(60) Provisional application No. 60/803,671, filed on Jun. 1, 2006.

(51) Int. Cl.
*H01J 35/06* (2006.01)
(52) U.S. Cl. .................................. 378/136; 378/138
(58) Field of Classification Search ............. 378/10, 378/122, 143, 136, 137; 250/492.21, 492.22, 250/492, 1
See application file for complete search history.

(56) References Cited

U.S. PATENT DOCUMENTS

| 4,447,732 | A | 5/1984 | Leung et al. |
| 4,793,961 | A | 12/1988 | Ehlers et al. |
| 5,198,677 | A | 3/1993 | Leung et al. |
| 5,945,677 | A | 8/1999 | Leung et al. |
| 6,094,012 | A | 7/2000 | Leung et al. |
| 7,084,407 | B2 | 8/2006 | Ji et al. |
| 2004/0051053 | A1* | 3/2004 | Barletta et al. ........... 250/492.1 |
| 2004/0141165 | A1* | 7/2004 | Zukavishvili et al. ......... 355/53 |

* cited by examiner

*Primary Examiner*—Hoon Song
(74) *Attorney, Agent, or Firm*—Lawrence Berkeley National Laboratory; Lawrence Edelman

(57) ABSTRACT

Techniques for controllably directing beamlets to a target substrate are disclosed. The beamlets may be either positive ions or electrons. It has been shown that beamlets may be produced with a diameter of 1 μm, with inter-aperture spacings of 12 μm. An array of such beamlets, may be used for maskless lithography. By step-wise movement of the beamlets relative to the target substrate, individual devices may be directly e-beam written. Ion beams may be directly written as well. Due to the high brightness of the beamlets from extraction from a multicusp source, exposure times for lithographic exposure are thought to be minimized. Alternatively, the beamlets may be electrons striking a high Z material for X-ray production, thereafter collimated to provide patterned X-ray exposures such as those used in CAT scans. Such a device may be used for remote detection of explosives.

19 Claims, 15 Drawing Sheets

Single Layer Switching

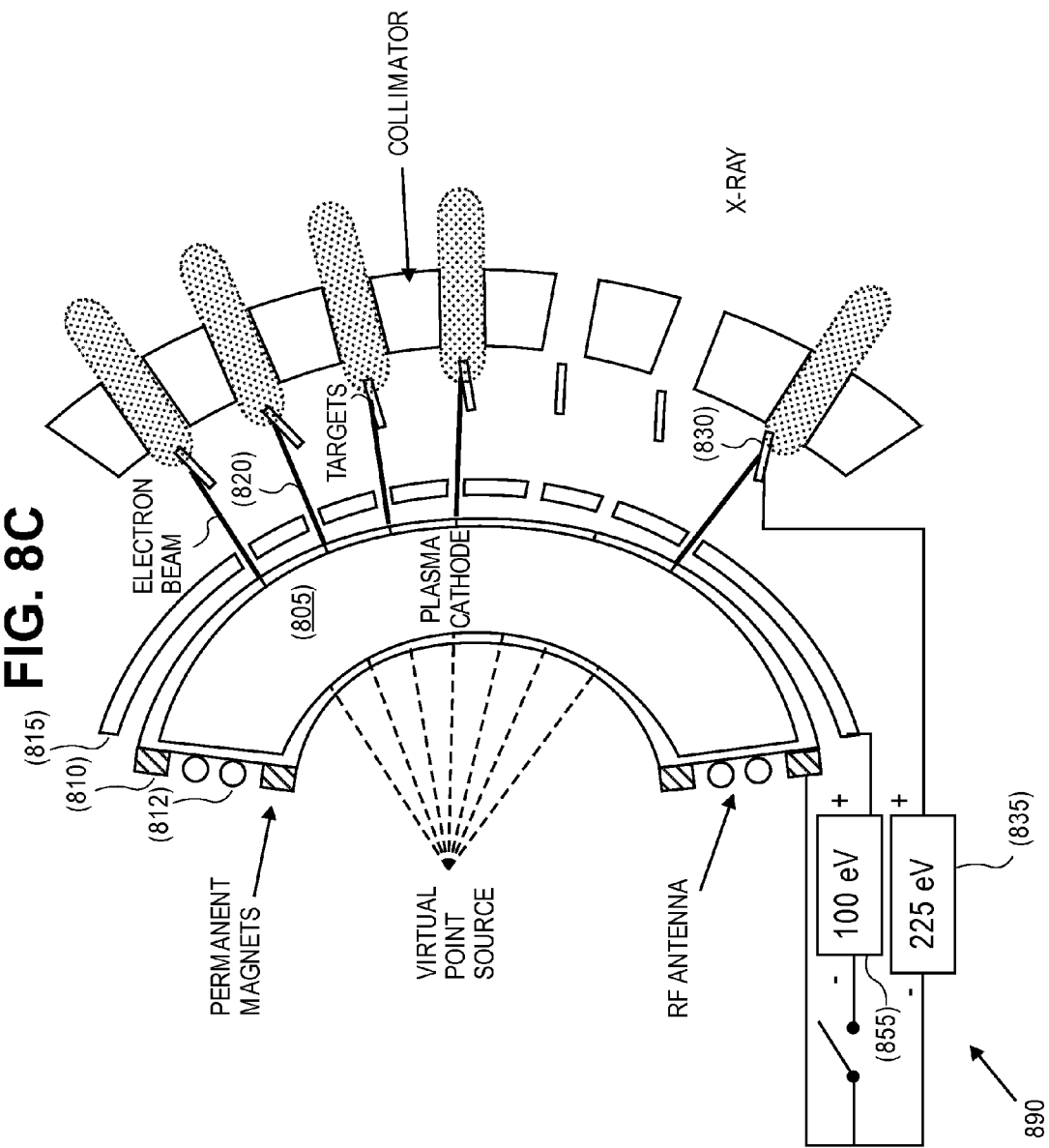

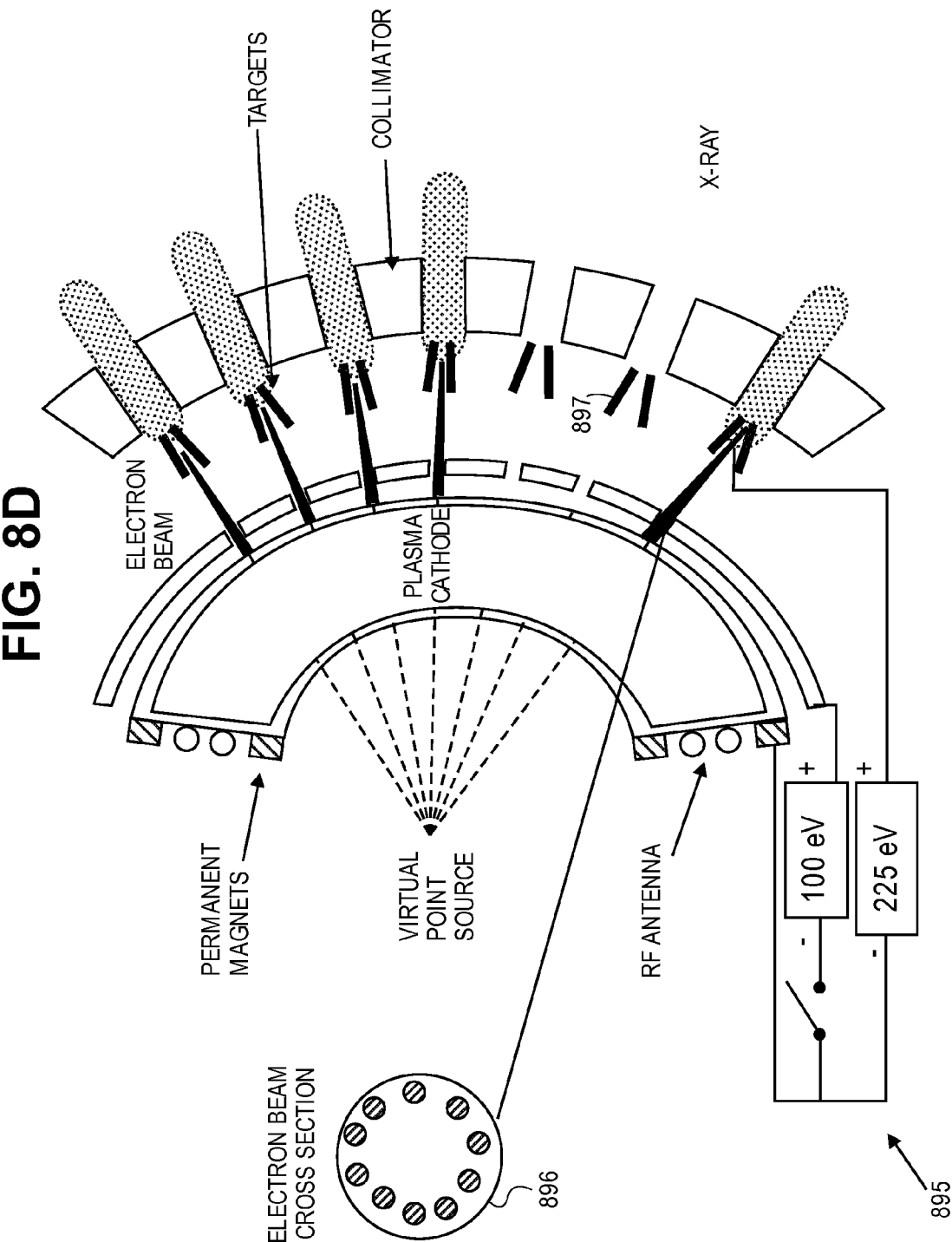

HIGH BRIGHTNESS—MULTIPLE BEAMLETS SOURCE FOR PATTERNED X-RAY PRODUCTION

CROSS REFERENCE TO RELATED APPLICATIONS

This patent application claims benefit of priority to U.S. Provisional patent application 60/803,671 filed Jun. 1, 2006, entitled "High Brightness and Multiple Beamlets Source for Maskless Lithography", which is hereby incorporated by reference in its entirety.

STATEMENT REGARDING FEDERAL FUNDING

This invention was made with U.S. Government support under Contract Number DE-AC02-05CH11231 between the U.S. Department of Energy and The Regents of the University of California for the management and operation of the Lawrence Berkeley National Laboratory. The U.S. Government has certain rights in this invention.

REFERENCE TO A COMPUTER PROGRAM

Not Applicable.

BACKGROUND OF THE INVENTION

1. Field of the Invention

The present invention relates generally to a high brightness and multiple beamlets X-ray source, more specifically to a high brightness and multiple beamlets X-ray source for patterned particle generation, and most specifically to a high brightness and multiple beamlets X-ray source for particle generation through a one-layer pattern generator. Alternatively, the invention may be scaled to generally relate for remote detection, more specifically to remote detection of explosives, and still more specifically to remote detection of certain chemical species.

2. Description of the Relevant Art

Photolithography Applications

As the dimensions of semiconductor devices are scaled down in order to achieve ever higher level of integration, optical lithography will no longer be sufficient for the needs of the semiconductor industry. Alternative "nanolithography" techniques will be required to realize minimum feature sizes of 0.1 µm or less. Therefore, efforts have been intensified worldwide in recent years to adapt established techniques such as X-ray lithography, extreme ultraviolet lithography (EUVL), and electron-beam (e-beam) lithography, as well as newer techniques such as ion projection lithography (IPL) and atomic-force-microscope (AFM) lithography, to the manufacture of 0.1 µm-generation complementary metal-oxide-semiconductor (CMOS) technology. Significant challenges exist today for each of these techniques: for X-ray, EUV, and projection ion-beam lithography, there are issues with complicated mask technology; for e-beam and AFM lithography, there are issues with low throughput.

Focused ion beam (FIB) patterning of films is a well-established technique (e.g. for mask repair), but throughput has historically been a prohibitive issue in its application to lithographic processes in semiconductor manufacturing. A scanning FIB system would have many advantages over alternative nanolithography technologies if it can be made practical for high volume production. Such a system could be used for maskless and direct (photoresist-less) patterning and doping of films in a semiconductor fabrication process. It would be necessary to focus the beam down to sub-µm spot sizes.

U.S. Pat. No. 7,084,407, filed Feb. 13, 2003, provides for a counter bored electrode capable of focusing an electron beam to small sizes, which is hereby incorporated by reference in its entirety.

U.S. Pat. No. 5,945,677 to Leung et al. issued Aug. 31, 1999 describes a compact FIB system using a multicusp ion source and electrostatic accelerator column to generate ion beams of various elements with final beam spot size down to 0.1 mm or less and current in the mA range for resist exposure, surface modification and doping.

Conventional FIB columns consist of multiple lenses to focus the ion beams. In order to get smaller feature size, small apertures have to be used to extract the beam and at the same time act as a mask. For the extraction of ions from a plasma source using a long, narrow channel, aberration is always a problem because of the edge effect.

Conventional multicusp plasma ion sources are illustrated by U.S. Pat. Nos. 4,793,961; 4,447,732; 5,198,677; 6,094,012, which are hereby incorporated by reference.

Additional remaining problems in the semiconductor field relate to the manufacture of masks, changing of masks, and registration of masks. A simpler technique would be to have an array of electron beamlets that can be controlled in such a manner so as to expose or block an ion or electron beam from a target wafer in production. Such array of electron beamlets could be stepped from device to device on the target wafer, or may be moved within a single device in precise positions.

Remote Detection Applications

Recent terrorist attacks have led to an elevated concern with regard to national and international security and have prompted security measures to be increased. These security measures, however, were not designed for scenarios in which individuals appear in an open environment and a security decision must be made at a distance from a suspected explosive. For scenarios such as these, standoff explosive detection is required; where physical separation puts individuals and vital assets outside of a zone of severe damage should an explosive device detonate. The difficulty of the standoff explosive detection task is exacerbated by several factors, including dynamic backgrounds that can interfere with the signal from the explosive, the potential for high false alarms, and the need to ascertain a threat quickly so that action can be taken [1]

Successful standoff explosives technology involves detection of a weak signal in a noisy environment. This background is also often dynamic, so that exemplary performance in controlled laboratory settings may be quite poor performance when applied in the field. The speed with which the detection is performed is a crucial factor when a potential threat is rapidly approaching. Finally, all explosives detection methods both generate alarms in the absence of threat, and do not alarm in the presence of a true threat. [1]

Standoff Compton backscatter X-ray detection system has been used to detect explosive, plastic weapons, and drugs. Using low-energy X-rays, the target is illuminated. Compton backscatter photons are collected that are subsequently emitted from the target. Photomultipliers detect light flashes in plastic that result from the backscatter photons. The image is assembled by scanning the X-ray over the target and detecting in synchronization the backscattered photons. Backscattered photons are produced relatively efficiently by substances of low atomic number. [1]

There is good potential for X-ray imaging at standoff distance of approximately 15 m. Research in the areas of high photon flux X-ray sources, pulsed X-ray sources, smaller focal spots for scanned beams, and focused X-ray beams can contribute to the successful development of standoff X-ray imagers. An alternative approach may be coded aperture imagers since they are able to achieve high sensitivities with practical devices.

BRIEF SUMMARY OF THE INVENTION

In one embodiment, this invention provides a method of patterned beamlet extraction, comprising: a) supplying a multicusp plasma source substantially containing a plasma; b) providing an extractor electrode adjoining the plasma, i) the extractor electrode comprising: (1) a plurality of apertures that pass through a conductive plasma side in direct contact with the plasma, (2) through an insulator, and (3) continuing through a conductive exit side; ii) the extractor electrode comprising one side of the multicusp plasma source; and c) controllably biasing the conductive exit side of one or more of the apertures in the extractor electrode to extract a pattern of beamlets according to the teachings of U.S. Pat. No. 7,084,407.

The exit side of any of the apertures may have a counter bore on the exit side (i.e. away from the plasma). The counter bored extraction system reduces aberrations and improves focusing. The invention also includes an ion source with the counter bored extraction system, and a method of improving focusing in an extraction system by providing a counter bore.

The method of patterned beamlet extraction above may have at least one of the extractor electrode apertures electrically connected with the conductive exit side as the aperture passes through the bulk insulator. The controllably biasing step in the extractor electrode may be relative to the conductive plasma side.

The method of patterned beamlet extraction may be used where the beamlets are positive ion beamlets or electron beamlets. Ion beamlets may be used for implantation with or without further acceleration, or used in ion projection lithography (IPL)

When electron beamlets are used, one may bias the electron beamlet target sufficiently high so as to produce X-rays at a specified certain energy. These X-rays may be collimated to form a collimated X-ray output.

The controllably biasing step discussed above may comprise: a) biasing the exit side of the extractor electrode so as to electrostatically pull the beamlet from the multicusp plasma source. The biasing the exit side step may comprise: applying to the exit side a relative voltage of greater than 10 volts higher than the plasma side to stop extraction of an ion beam from the extractor. Alternatively, the biasing the exit side step may comprise: applying to the exit side a relative voltage of more than −5 volts lower than the plasma side to extract an electron beam from the extractor.

The beamlet apertures may be about 1 µm in diameter, and spaced 12 µm or greater apart. The extractor may have a thickness of at least one of the group consisting of: 20 µm, 10 µm, and 5 µm.

The beamlets may be directed to a target substrate, such as a wafer used in photolithography. In this case the method of patterned beamlet extraction may be used for processing the target substrate with standard photolithographic techniques to allow for maskless photolithography for either ion- or e-beam-sensitive photoresists.

Alternatively, the method of patterned beamlet extraction may comprise biasing the target substrate relative to the plasma to allow for maskless ion implantation. Here, the ion to be implanted is one of the species present in the multicusp plasma source.

All of the methods discussed above may be embodied into a device for patterned beamlet extraction.

In another embodiment, a device for patterned beamlet extraction may comprise: a) a multicusp ion source having a plasma; b) computer controlled means whereby selectable patterns of beamlets are extracted from the plasma.

The device for patterned beamlet extraction may comprise: a) a target biased relative to the plasma to impinge at least one of the electron beamlets upon to produce X-rays; and b) a collimator proximally located to the target, whereby collimated patterned X-rays are produced. Furthermore, a substrate may be positioned to be exposed by the collimated patterned X-rays, which is thereby exposed without a mask.

In another embodiment, a device for remote scanning may comprise: a) a multicusp ion source having a plasma; b) computer controlled means whereby selectable patterns of collimated X-rays are produced from electron beamlets extracted from the plasma. In this device, there may also be: a) a detector disposed to detect X-ray transmission and scatter from the selectable patterns of collimated X-rays as the X-rays pass through a test subject; and b) a computer to analyze data input from the detector so as to provide a computed axial tomograph (CAT) scan.

In still another embodiment, the device for remote scanning may analyze Compton backscatter when the detected X-ray data is temporally distinct from excitation X-rays generated at a specified energy.

BRIEF DESCRIPTION OF THE SEVERAL VIEWS OF THE DRAWINGS

The invention will be more fully understood by reference to the following drawings, which are for illustrative purposes:

FIG. 8C is a schematic of a virtual point source embodiment of a spherical section of a high flux, coded X-ray source with radial X-ray targets and collimators.

FIG. 8D is a schematic of a virtual point source embodiment of a spherical section of a high flux, coded beamlet X-ray source with radially disposed truncated cone X-ray targets and collimators.

DETAILED DESCRIPTION

Figure 1A:
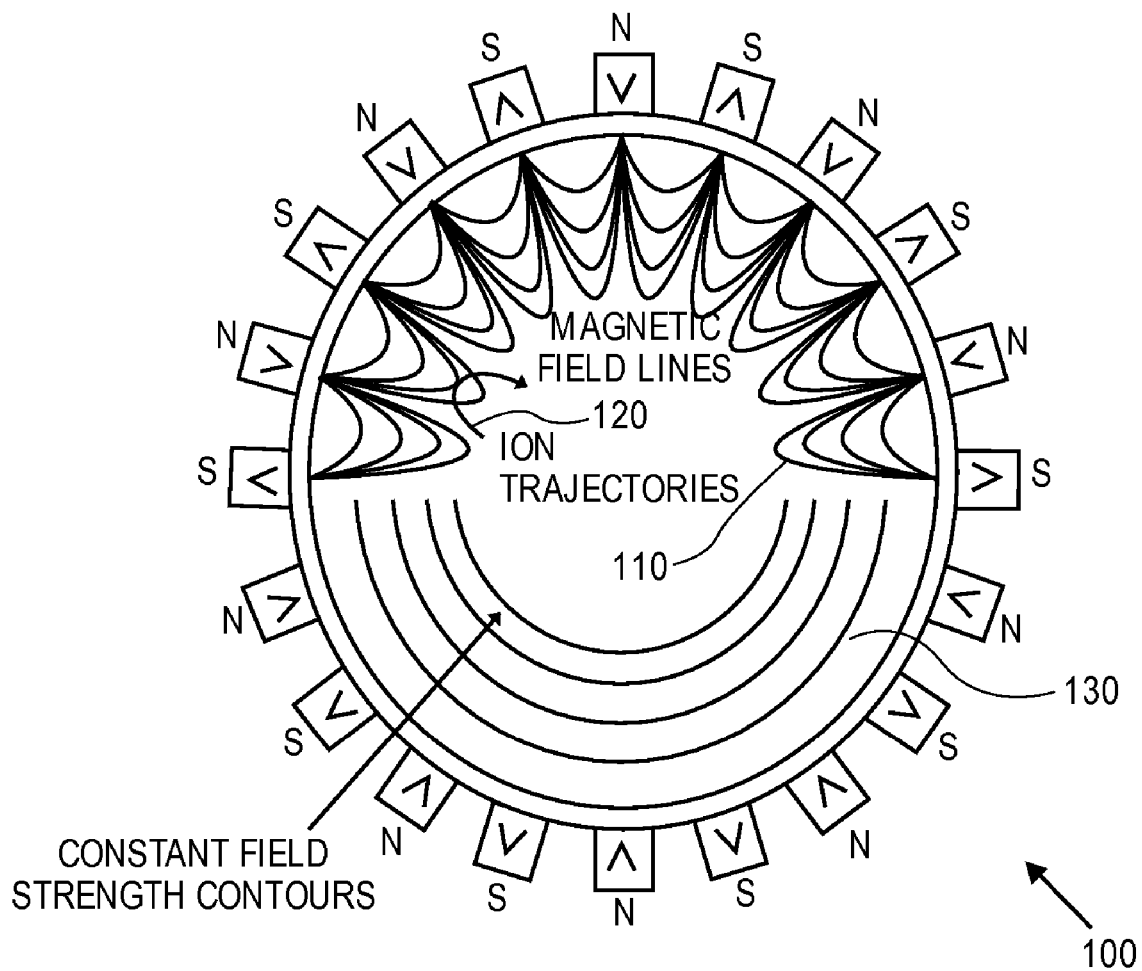
FIG. 1A is a multicusp plasma generator.

Definitions
DC means direct current.
RF means radio frequency.
Coded means programmable, selectable, or programmable, such that in an electrode array may be selectably addressed at the one pixel or group of pixels level for patterned operation. Pixels may be simultaneously or sequentially addressed as needed for a given application.
μm means micron, or $10^{-6}$ meters.

Introduction

This application discusses methods of generation of multiple electron beamlets. Such system may be used in the generation of ion beamlets by suitable modification of the plasma source and extraction voltages. High brightness electron beamlets may strike an X-ray generating target to in turn produce high brightness X-ray sources. These X-ray sources may be collimated, or act as point sources with spherical radiation patters.

By a suitable choice of source plasma, ions may be extracted in high brightness beamlets to impinge on a target such as Ti to produce neutrons or gammas as desired by suitable configuration of plasma ion species and extraction voltages through appropriate inertial fusion reactions.

Each of the beamlets, or indeed small groupings of beamlets, may be individually or simultaneously selected for operation, thus forming a coded source. When electrons are generated with no intervening target, such overall device may operate as a high brightness electron lithography writing (or exposure) system with or without focusing of individual beams or beamlets as taught in U.S. Pat. No. 7,084,407, hereby incorporated by reference.

In alternate embodiments, the extraction geometry may be substantially planar, convex, or concave. In a concave application, a group of coded X-ray sources may be used as sources for computed axial tomography (CAT). In convex applications beams may be sent out radially in a pattern to illuminate a region of interest. Detectors may then be used to form images of samples interspersed between the beam sources and detectors.

In the sections below, two predominant applications will be explored: 1) direct beamlet lithography, and 2) remote detection.

Multiple Electron Beamlets with High Brightness

For both electron beam project lithography systems and electron beam inspection tools, large area electron sources, which can produce multiple electron beamlets with high brightness, are essential. Carbon-nanotube field emission tips have shown progressive results in producing multiple electron beamlets. However, homogeneity of the emission, control of the emitter orientation and dimension, and high current degradation are three prohibitive factors for large volume semiconductor manufacturing. In order to circumvent these issues, a large area, high brightness plasma cathode is desirable. Both DC-filament discharge and RF-driven multicusp plasma sources developed at the Lawrence Berkeley National Laboratory can produce uniform plasma over a large area, therefore a single source may be used to generate a large number of closely packed beamlets for parallel processing—an advantage which cannot be found in any other type of plasma generator. The constituents of the plasma are ions and electrons, as well as non-ionized neutrals. By changing the polarity of the extraction system, either positive ion or electron beams can be extracted. This type of plasma can generate electron beams at high current density. It has been shown that the electron temperature and therefore the axial electron energy spread of the multicusp source can be as low as 0.1 eV using a permanent-magnetic filter—which is essential to produce low energy electron beam.

FIG. 1A depicts a multicusp plasma source 100 showing magnetic field lines 110 and typical ion trajectories 120 as a result of the field lines 110. Here it is shown that field strength contours are generally radially constant 130.

Figure 1B:
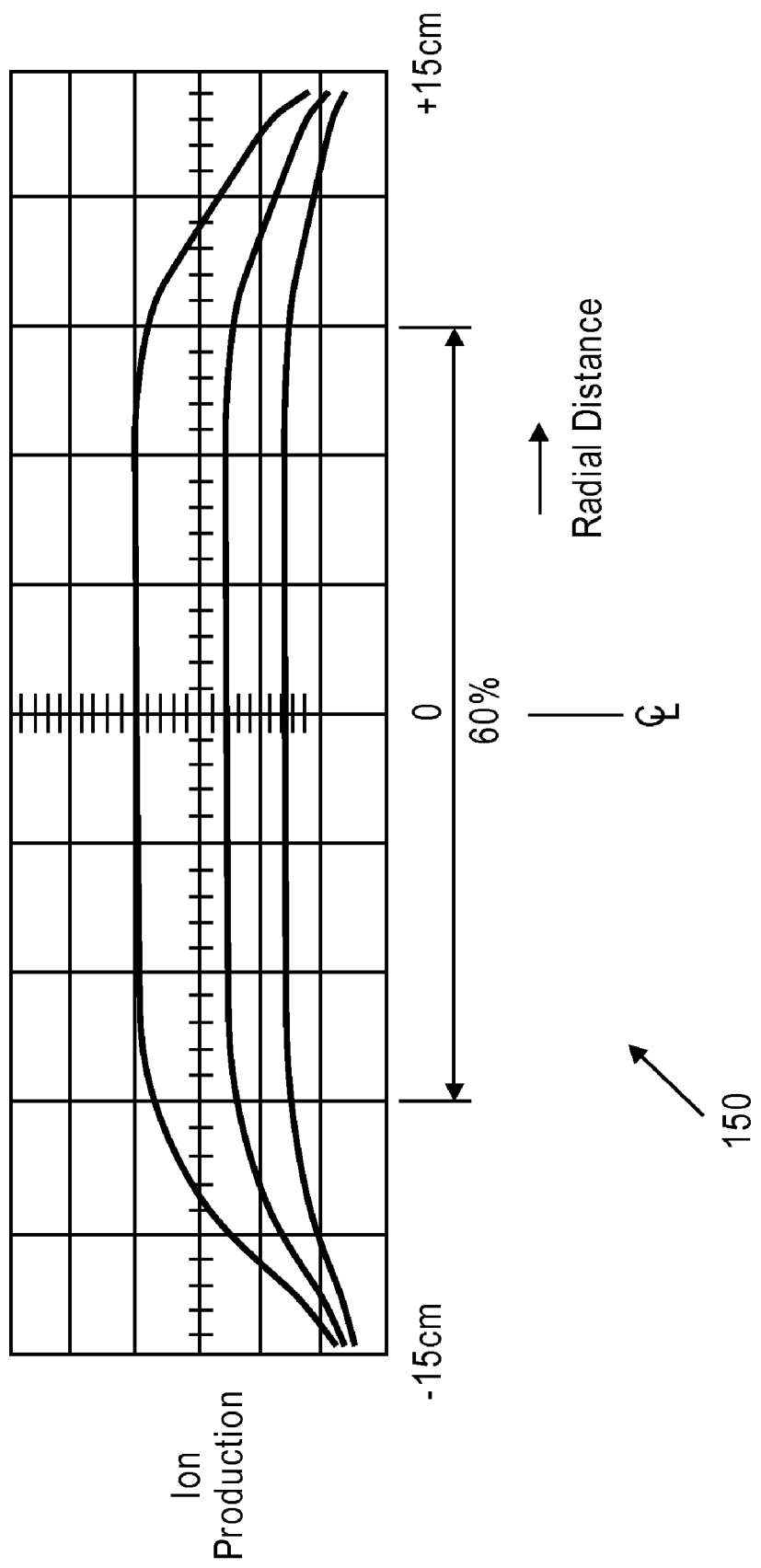
FIG. 1B is a radial density profile for the multicusp plasma generator of FIG. 1A.

FIG. 1B shows a plot 150 of radial electron or plasma production over a width of 30 cm. The plot 150 indicates that electron or plasma (labeled "Ion") production is very constant in magnitude over about 60% of the diameter of the source.

Figure 2:
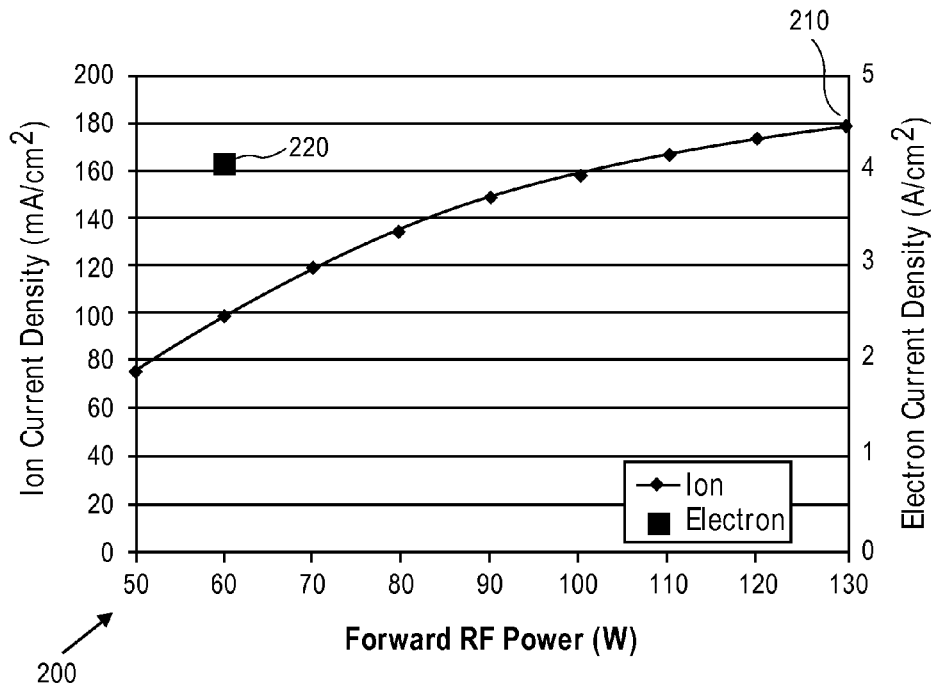
FIG. 2 shows a current density of a single electron beam at the source side produced by a small RF-driven plasma cathode.

FIG. 2 is a graph 200 of current density vs. forward RF power of a single electron beam at a source side produced by a small RF-driven cathode. The graph indicates a maximum 210 of about 180 mA/cm$^2$ ion current density at 130 W of RF power. Similarly, maximum electron current density 220 is achieved of about 4.5 A/cm2 at 60 W of input RF power.

Figure 3:
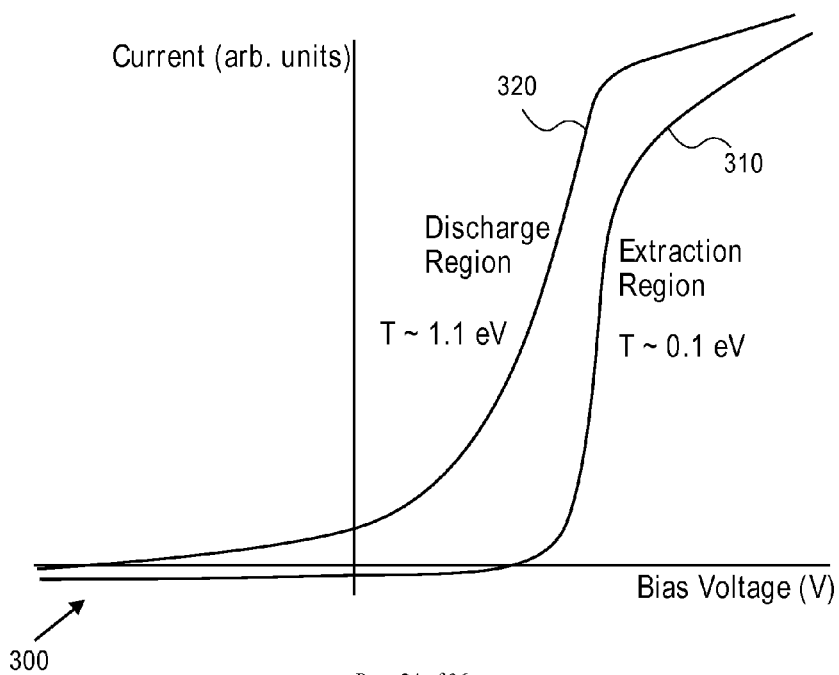
FIG. 3 shows Langmuir probe traces of the discharge and extraction region, indicating that electron temperatures at the extraction region are much lower than at the discharge region.

FIG. 3 is a graph 300 of Langmuir probe traces of the discharge and extraction regions. This graph 300 is of current in arbitrary units versus bias voltage. It is noted that electron temperatures 310 at the extraction region is much lower than at the discharge region 320.

Figure 4A:
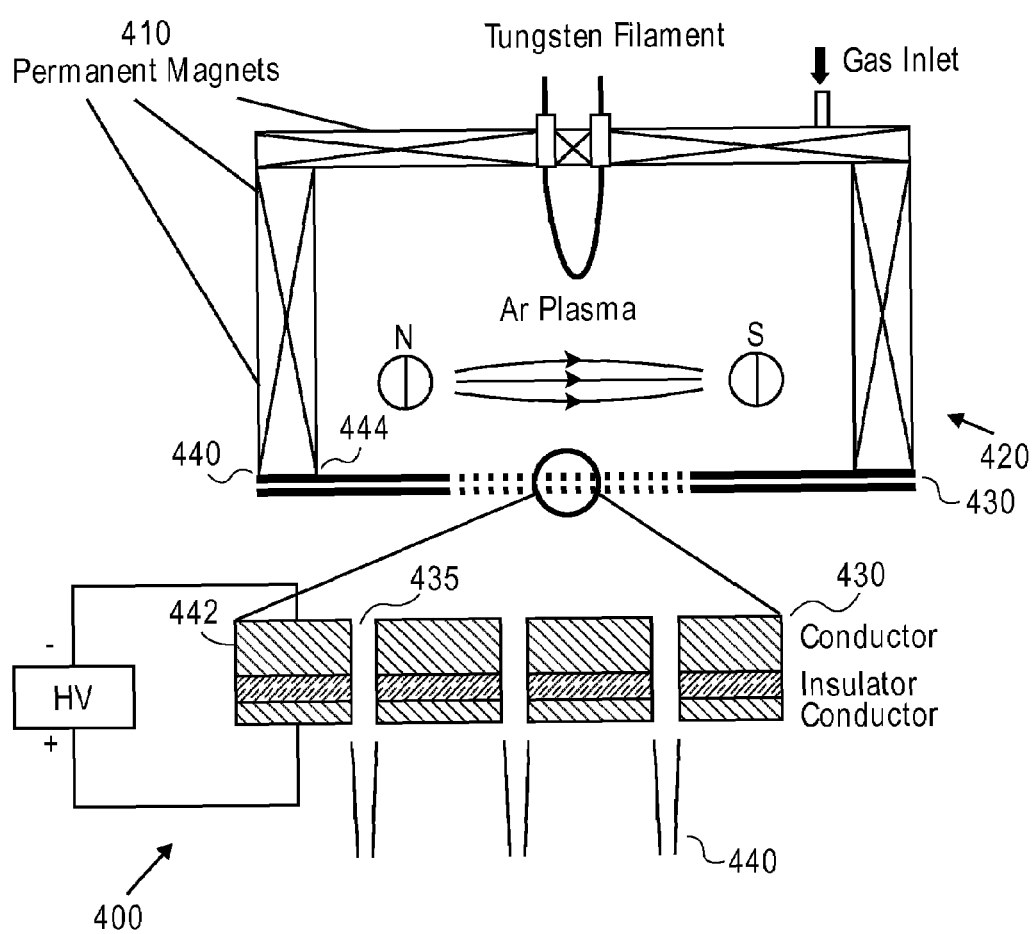
FIG. 4A shows a DC-filament discharge plasma cathode.

FIG. 4A shows a DC-filament discharge plasma cathode configuration 400 of a high brightness multiple beamlets electron source. A permanent magnetic filter 410 is installed in the plasma cathode 420 in order to achieve low electron temperature and low axial energy spread. An extraction element 430 consisting of a conductor-insulator-conductor membrane with multiple apertures 435 is used to generate multiple electron beamlets 440 when so selected. During normal operation, the metal film on the topside 442 is connected to the source chamber 444. One can control the current of the electron beams 440 by applying a positive bias voltage 446 through the connecting wires on the bottom surface.

Figure 4B:
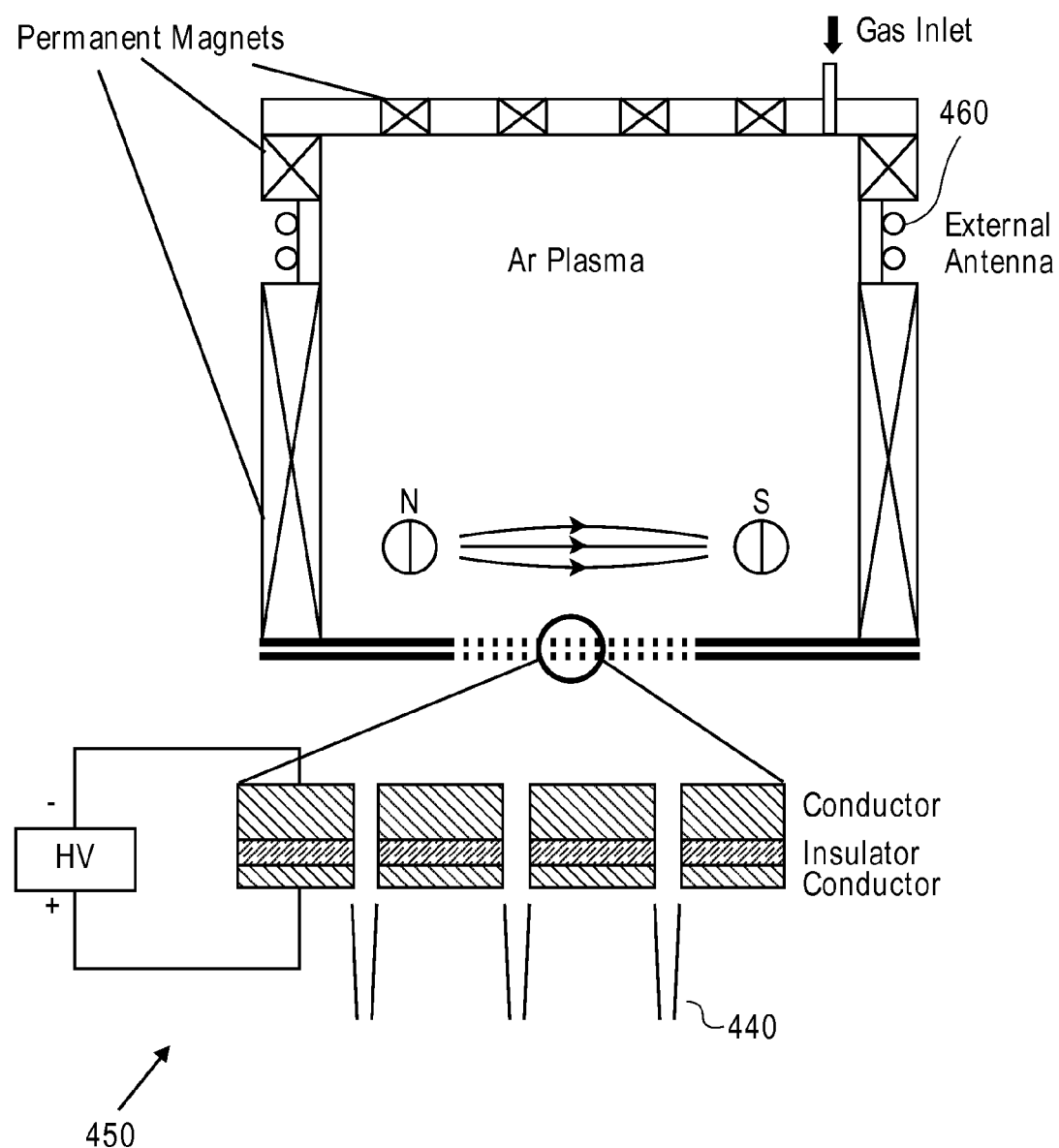
FIG. 4B shows a plasma cathode with external RF-antenna.

FIG. 4B shows a high brightness multiple beamlets electron source 450 where the plasma cathode has an external RF-antenna. This device shares many similarities with that of FIG. 4A, so those details are not repeated, and are instead incorporated by reference. Here, an external antenna 460 provides RF input power to the source. As above, an extraction element consisting of a conductor-insulator-conductor membrane with multiple apertures is used to generate multiple electron beamlets. During normal operation, the metal film on the topside is connected to the source chamber. One can control the current of the electron beams by applying a positive bias voltage through the connecting wires on the bottom surface.

Figure 4C:
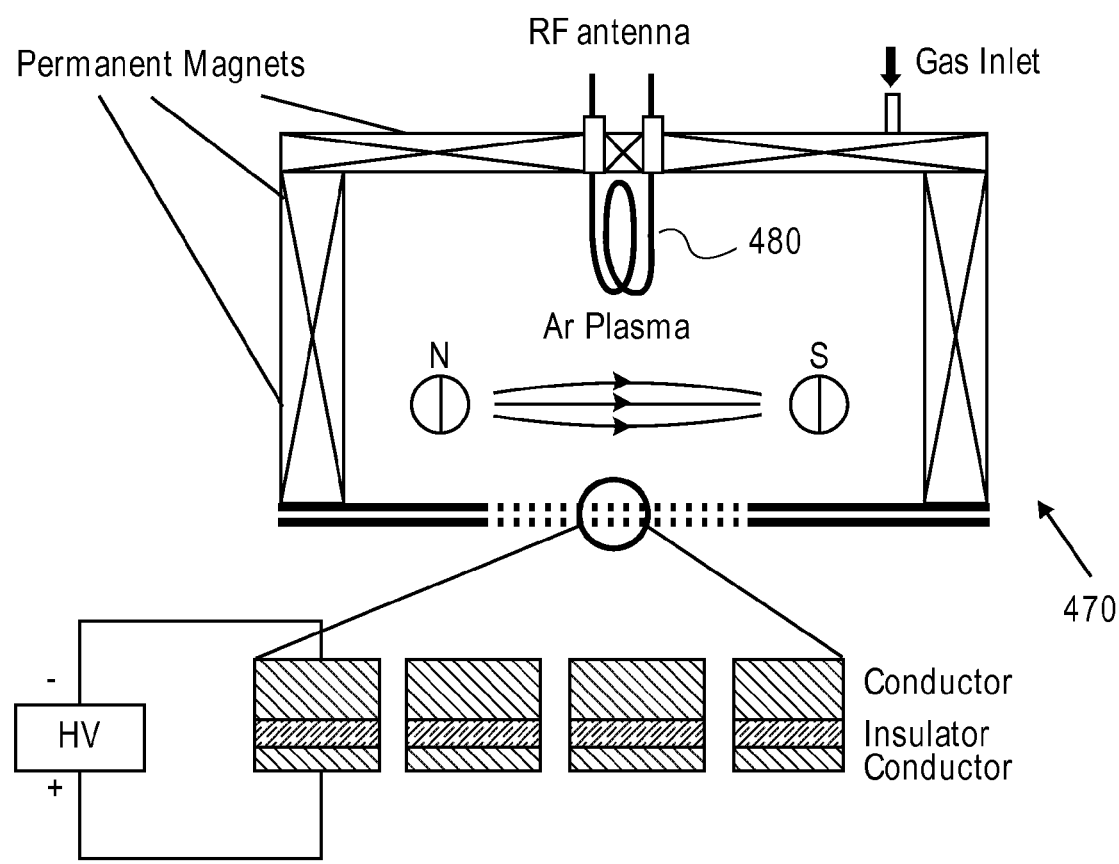
FIG. 4C shows a plasma cathode with internal RF-antenna.

FIG. 4C shows a high brightness multiple beamlets electron source 470 where the plasma cathode has an internal RF-antenna 460. This device shares many similarities with those of FIGS. 4A and 4B, so those details are not repeated, and are instead incorporated by reference. Here, an internal RF antenna 480 provides RF input power to the source. As above, an extraction element consisting of a conductor-insulator-conductor membrane with multiple apertures is used to generate multiple electron beamlets. During normal operation, the metal film on the topside is connected to the source chamber. One can control the current of the electron beams by applying a positive bias voltage through the connecting wires on the bottom surface.

EMBODIMENTS OF THE INVENTION

Bulk Processing

In the embodiment of the invention described above, bulk processing of materials with high brightness and multiple beamlets of ion or electron beams is possible. Thus, fast processing may be done due to the high brightness of the beams. Alternatively, the extractor may be a single mask with apertures only in selected regions for processing of the pattern inherent in the mask. Although this is not as flexible as the addressably coded approach described below, it may be preferable for some implementations.

Maskless Lithography

For maskless ion beam lithography, ions are supplied by a low axial energy spread plasma source as described above with large areas of uniform current density. The patterns are generated by switching the individual beamlets on or off in the extraction element. The combined beamlets are then accelerated and projected onto (for instance) a resist coating on the target wafer or other target. Subsequent processing of the target wafer may be done as in traditional photolithography, but here it has been maskless electron beam lithography.

Beamlet switching has been achieved by using a pattern generator which consists of three layers of electrodes—that is two metallic with an insulating electrode in between. The aperture is about 1 μm in diameter. By biasing the third electrode ~10 volts more positive than the first electrode, the ion current of the individual beamlet can be turned off. This beamlet switching technique has been demonstrated experimentally with a pattern generator that contains large diameter apertures. A pattern generator with 1 μm aperture and with total thickness greater than about 20 μm is very difficult to construct. In order to overcome this challenging technical problem, a single-layer pattern generator system has been designed. This resulting arrangement appears much simpler and may be easily constructed with traditional electron beam writing devices. Such traditional electron beam writing devices have been used for mask generation in the past, circuit or mask repair, and other uses.

Figure 5:
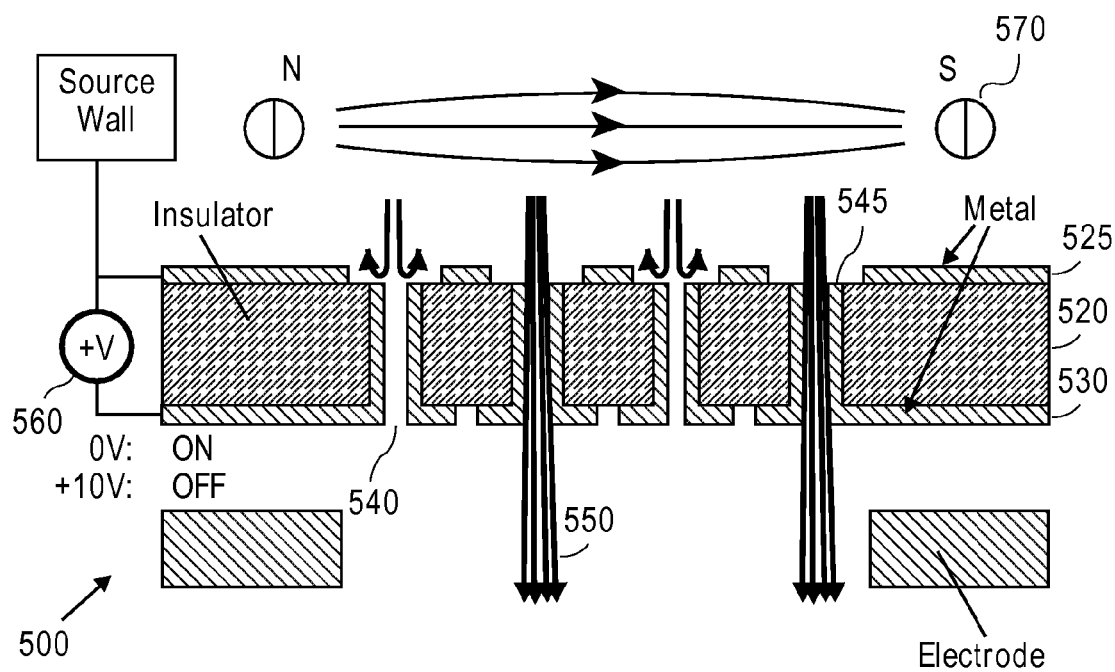
FIG. 5 shows a pattern generator with controlled apertures for maskless lithography and other applications.
Figure 5:
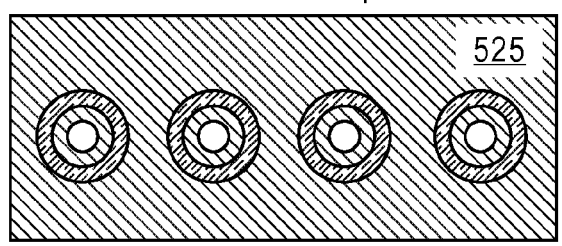
Figure 5:
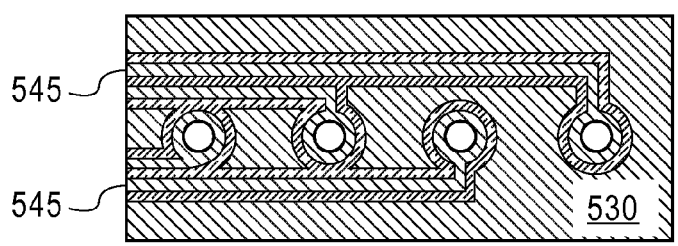

FIG. 5 shows the arrangement of the resultant e-beam pattern generator 500. It is installed just below the magnetic filter 510 as the extraction element discusses above. It consists of ~20 μm thick insulating layer 520 such as silicon dioxide. The top 525 and the bottom side 530 of this insulating layer as well as the inner surface of the aperture 540 channel are metalized as shown in FIG. 5. During normal operation, the metal film on the top 525 and the bottom 530 side are connected to the source chamber while the metal layer 545 in the aperture channel 540 can be biased individually with respect to the chamber wall 444 (shown in FIG. 4A). Thus one can control the current through each beamlet 550 by applying a positive bias voltage 560 through the connections 545 on the bottom surface 530.

Figure 6A:
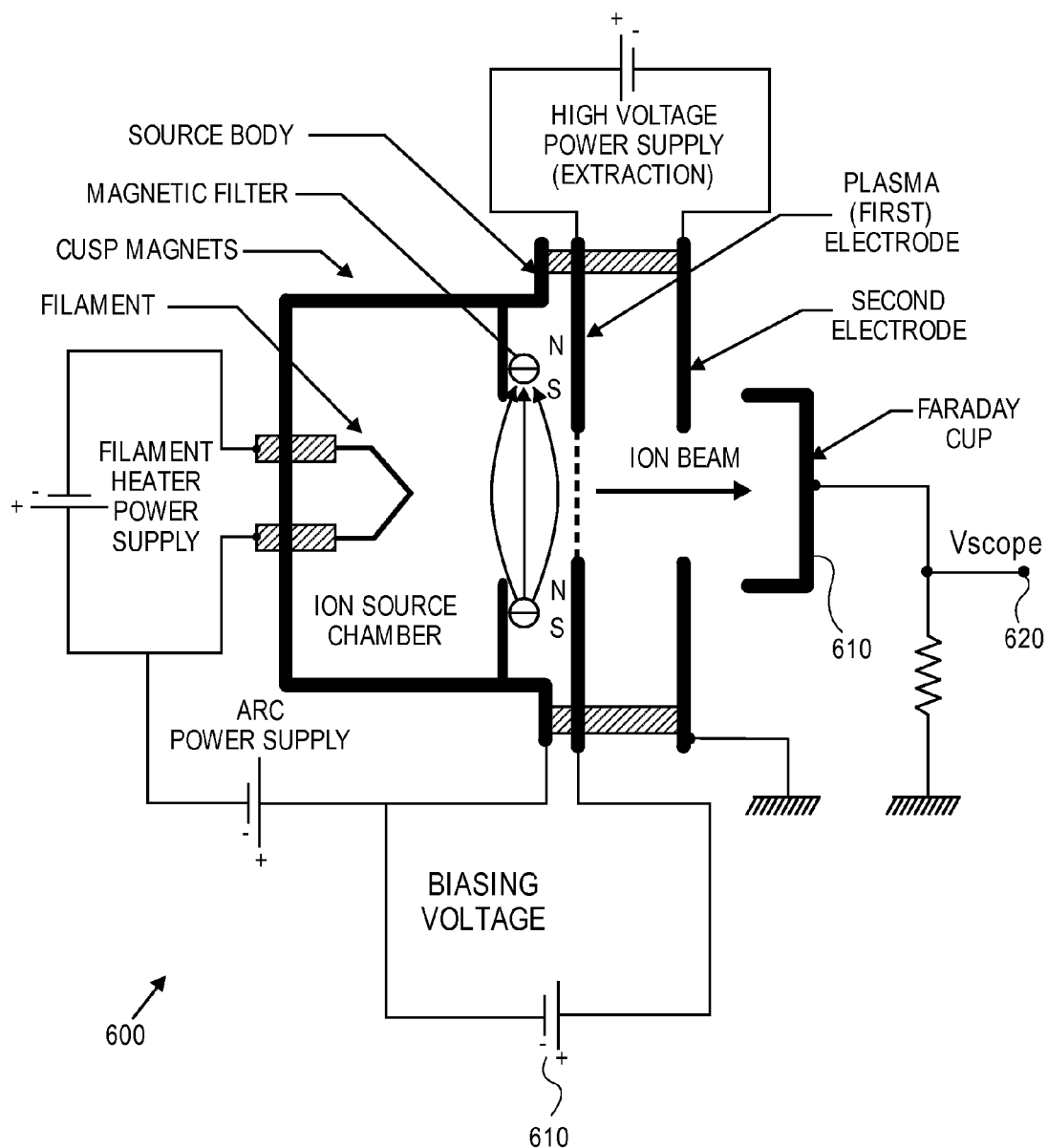
FIG. 6A is a schematic diagram of an overall extraction test system with a Faraday cup to detect the ion beam current.

FIG. 6A is a schematic diagram of an overall test system 600 with a Faraday cup 610 measuring the electron beam current at a $V_{scope}$ test point 620.

Figure 6B:
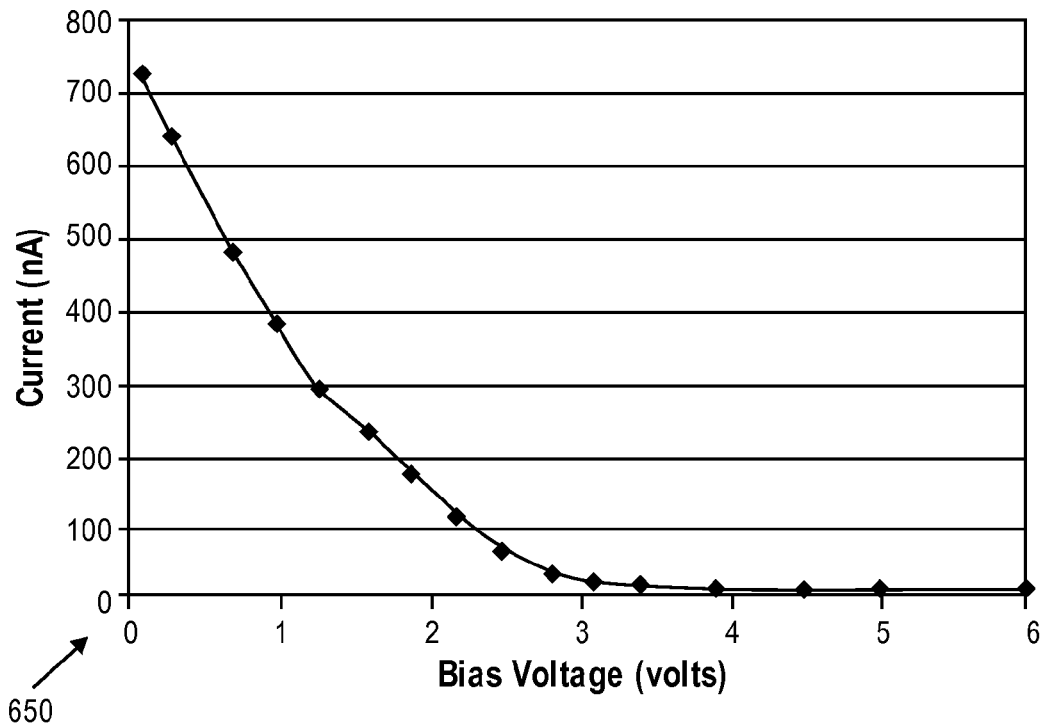
FIG. 6B is a graph of measured beam current in the configuration of FIG. 6A versus bias voltage. It appears that about a 5 volt bias is necessary to turn the beamlet current off.

FIG. 6B shows a plot 650 of beam current in nA versus bias voltage 630 (shown in FIG. 6A) in volts. It appears that about a 5 volt bias 630 is necessary to turn the beamlet current completely off.

Figure 6C:
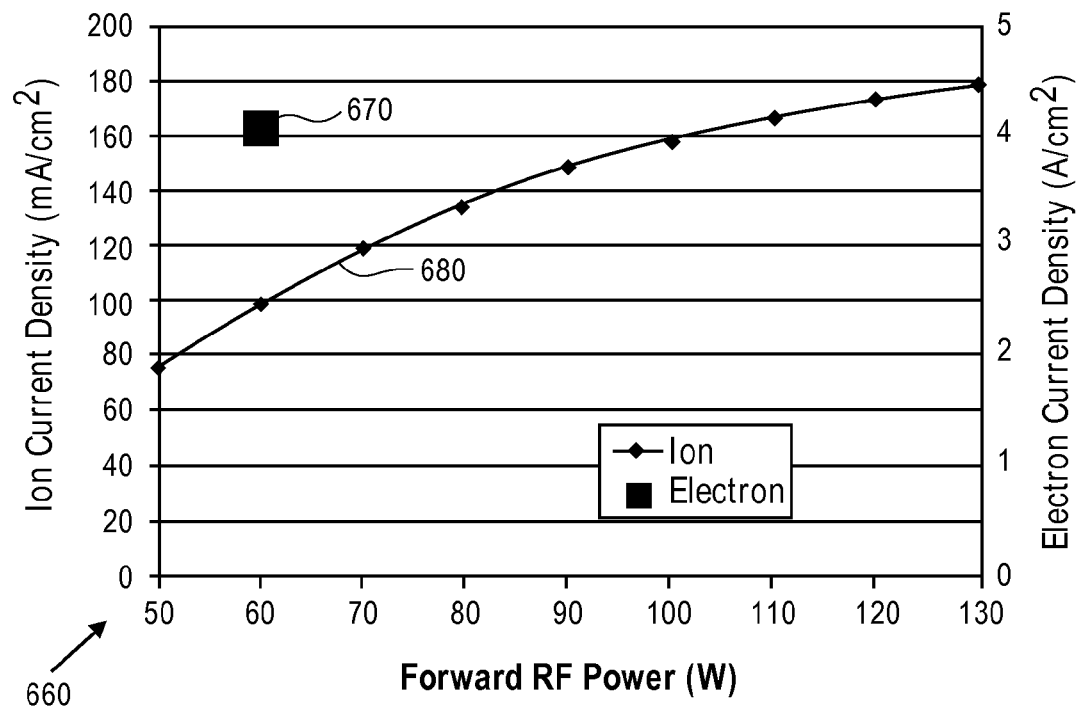
FIG. 6C is a graph of measured beam current density of a single electron beam in the configuration of FIG. 6A versus forward RF power produced by a small RF-driven plasma cathode.

FIG. 6C shows a plot 660 of the current density versus RF power of a single ion beam at the source side produced by a small RF-driven plasma cathode for both and electron beam 670 and an ion beam 680.

Figure 7A:
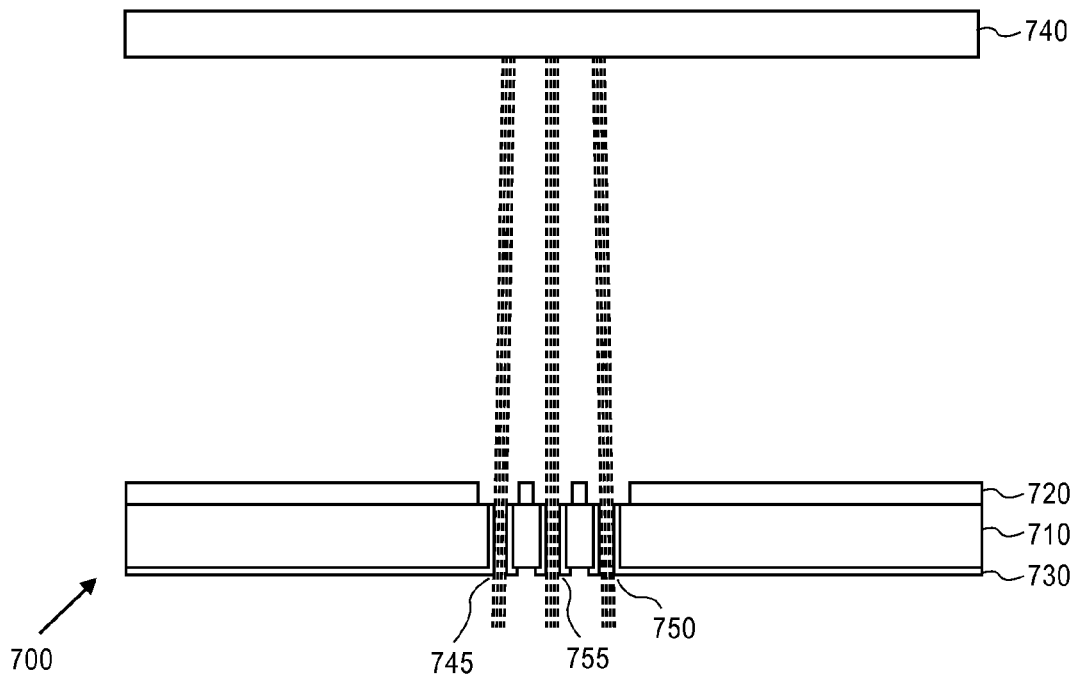
FIG. 7A is an ion optics simulation showing the by-stander effect of biasing the aperture. It can be seen that by applying a positive bias on one aperture, the current through the neighboring apertures are not affected.

FIG. 7A is an ion optics simulation 700 showing the bystander effect of biasing the aperture. Here the main support insulator 710 is modeled as 20 μm thick. On the plasma side is a 5 μm thick metal conductor 720 at about 0 V. On the exit side of the conductor 710 is a 1 μm thick metal conductor 730 biased at about −5 V. It can be seen that by applying a positive bias on one aperture 745, the beam paths 750, 755 through the neighboring apertures (which are also turned on) are not affected. The electrode 740 is at approximately 10 V for this simulation.

Figure 7B:
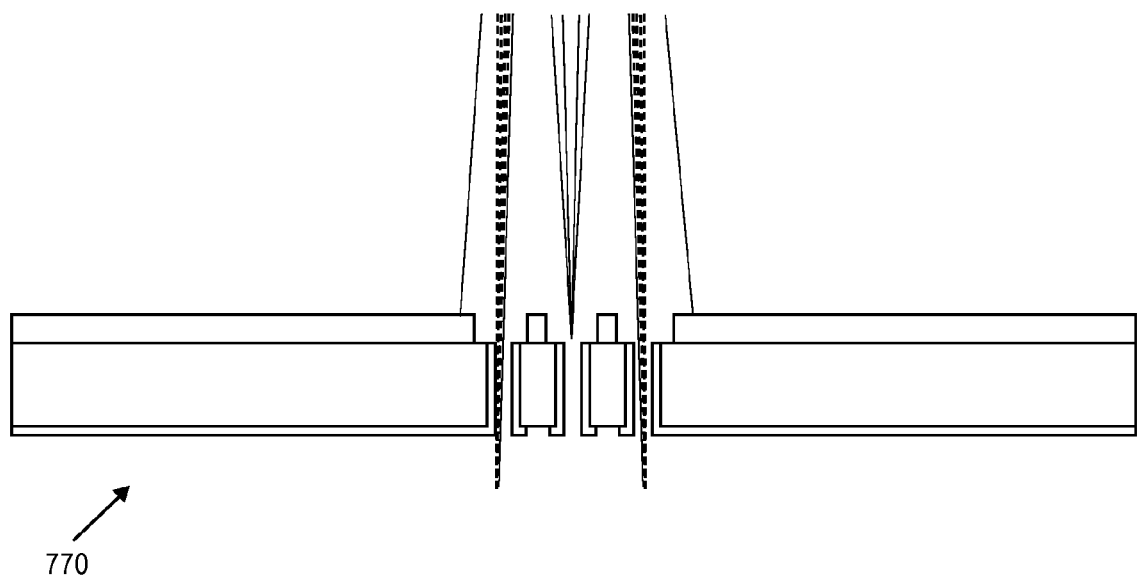
FIG. 7B shows that switching the beamlets on and off is independent of adjacent beamlets. Such arrayed switching, either alone, or coupled with a translational movement of the target substrate relative to the maskless pattern generator, may be used to form any desired pattern on the target substrate.

FIG. 7B is an ion optics simulation 770 that shows that switching the beamlets on and off is independent of adjacent beamlets. Such arrayed switching, either alone, or coupled with a translational movement of the target substrate relative to the maskless pattern generator, may be used to form any desired pattern on the target substrate.

FIGS. 8A-8D and 9 show differing configurations of patterned (or coded) X-ray sources. These will be described in further detail below.

Figure 8A:
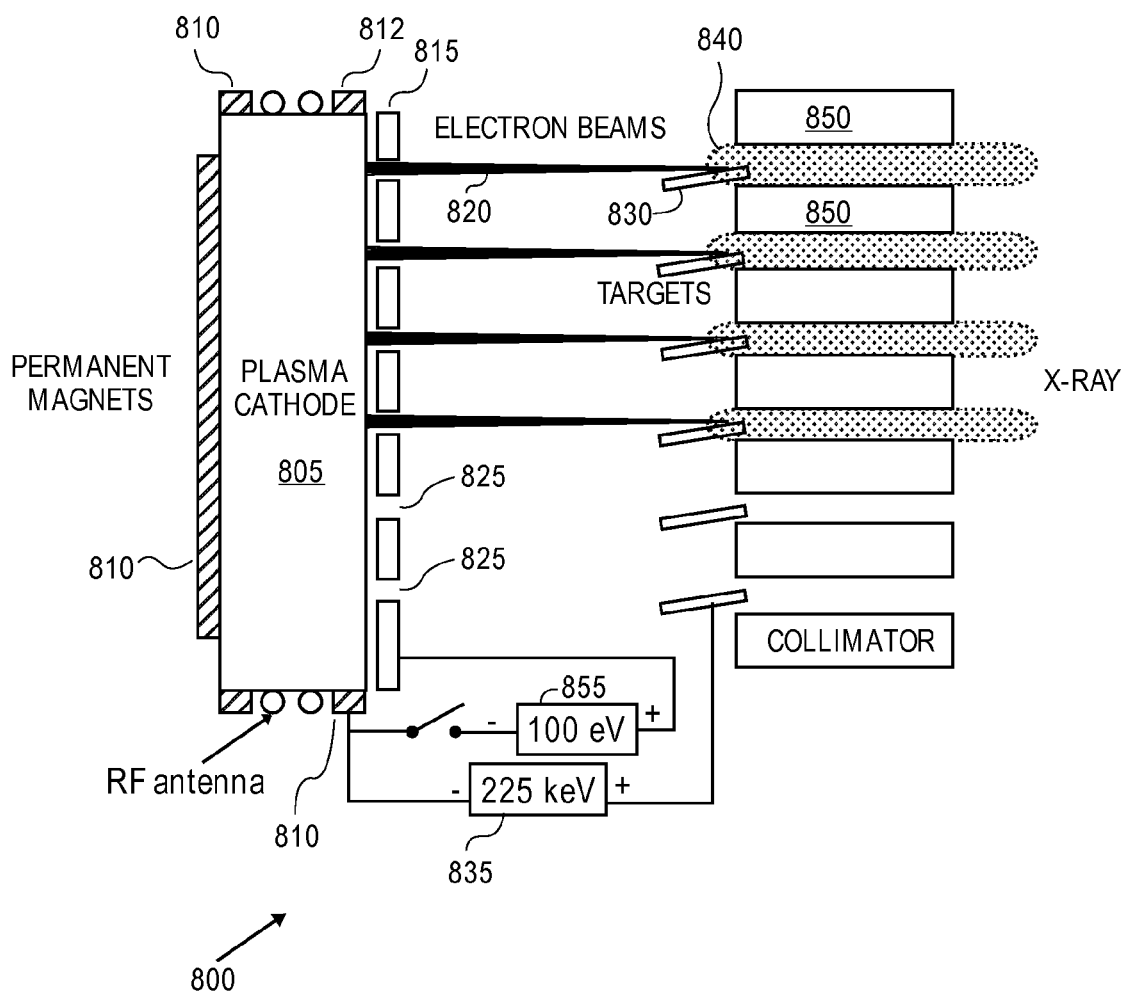
FIG. 8A is a schematic of a linear embodiment of a high flux, coded X-ray source.

Referring now to FIG. 8A, a schematic diagram of a planar patterned X-ray source 800 is described. Here, a plasma cathode 805 acts as an electrode source, with permanent magnets 810. The plasma cathode 805 either a DC-filament discharge or RF-driven multicusp plasma source, typical of those developed here at Lawrence Berkeley National Laboratory. In this example, the RF antenna 812 drives the multicusp plasma source. The plasma cathode 805 here is used as a single source to generate a large number of closely packed beamlets for parallel processing—an advantage which cannot be found in any other type of plasma generator. The constituents of the plasma are ions and electrons, as well as un-ionized neutrals. By changing the polarity of the extraction system, either positive ion or electron beams can be extracted. However, for the patterned X-ray generation application, only electron beams are used. This type of plasma can generate electron beam at high current density as previously described.

Selectively patterned electrodes 815 are in this instance selected to produce only the four upper beams 820, while the two lower beam positions are selected in the "off" position. The "on" beams 820 proceed to electron targets 830, where if the accelerating voltage 835 is sufficient, X-rays 840 are produced. To control the application of the X-rays 840, one collimator 850 allows only a collimated beam of X-rays 855 to emerge. The collimators may be a high Z material for X-ray absorption, and may be of a sufficient length to width ratio to produce spot sizes as required on a target (not shown). A collimator with multiple channels can be used to generate multiple "pencil" X-ray beams as desired.

Since the "on" and "off" voltage swing 855 is here only 100 v, it is easy to selectively emit pulses of X-rays in a short pulse, controllable manner. Here, even the accelerating voltage 835 may be varied to match the application. Thus, it is possible to produce time limited pulses approximating a "gray scale" of X-ray deposition similar to a pixilated display screen. Each or all of the electron beams can be sequentially switched on to produce coded X-ray or switched on simultaneously to produce encoded operation mode.

FIG. 8A is only a linear cross section of what may be a two dimensional planar device. Where the selection electrodes 815 are patterned in a two dimensional addressable array configuration, virtually any size area may be controllable written in a pixel by pixel fashion by the patterned X-ray generator. In fact, when the apparatus 800 is arranged to illuminate a suitable X-ray scintillating material, an equivalent to a gray scaled monochrome display monitor would be possible to verify correct operation of the addressable X-ray source 800.

Figure 8B:
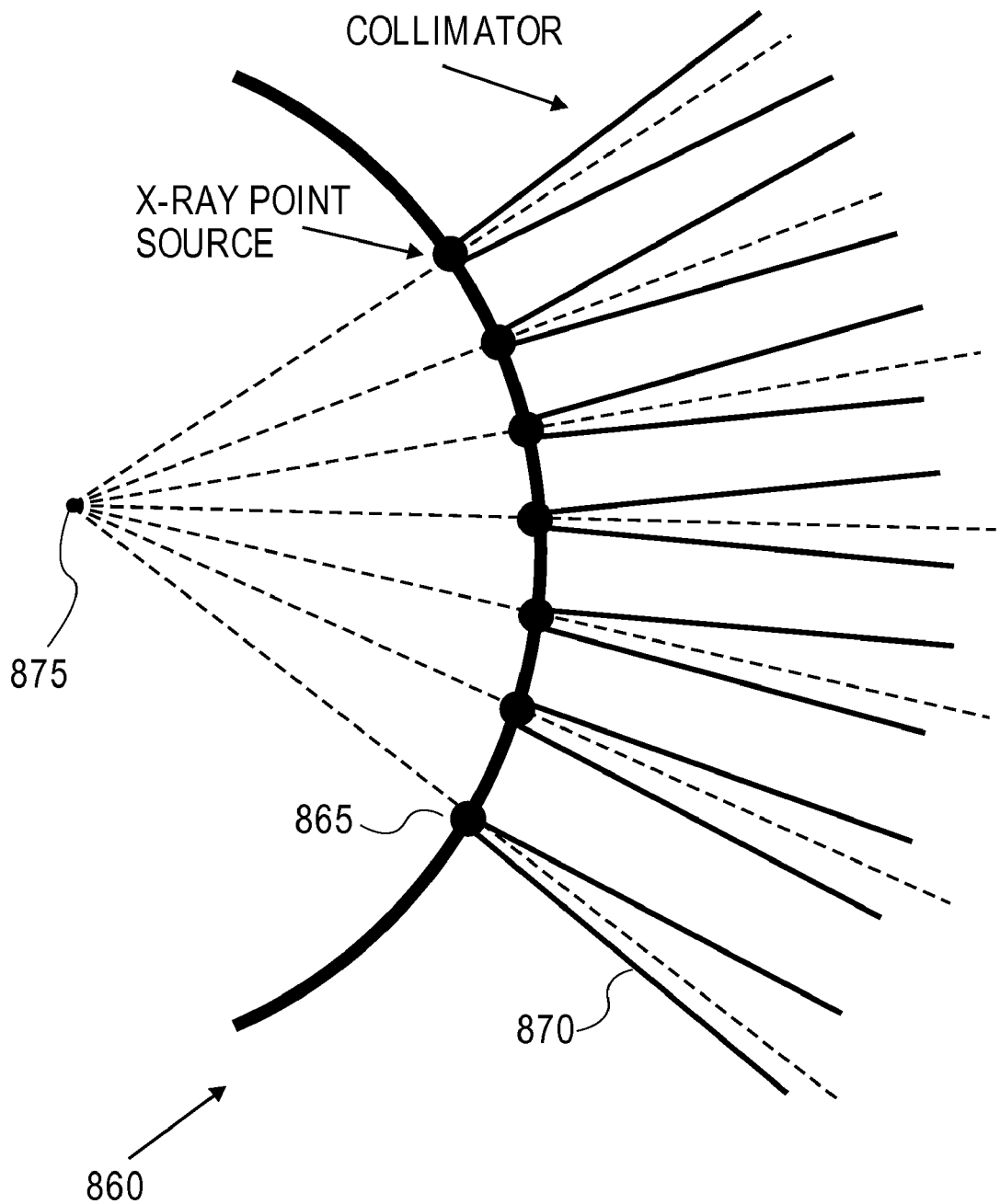
FIG. 8B is a schematic of a virtual point source embodiment of a high flux, coded X-ray source.

FIG. 8B essentially shows a convex X-ray source 860, where a plasma source, programmable extraction electrode, accelerating electrode, and target (these are shown in detail later in FIG. 8C, and are very similar to those of FIG. 8A) work together to essentially form set of addressable X-ray point sources 865. Here electron beams can also be extracted from a curved surface. All the X-ray point sources seem to be emitted from a virtual point 875. Each point source has uniform emission and the number of pointed source can be optimized. Since the electron beams are operated at pulsed mode, each point source can be operated (pulsed) with more than an order of magnitude higher flux than a single continuously operating point source that is limited by a maximum 2 kW/mm² power density due to thermal limitations (target melting). Suitable matched conical collimators 870 allow for the production of addressably collimated X-rays all having a common virtual source location 875. Although FIG. 8B shows just a radial arc as a cross section, actual implementations could be cylindrical or spherical in overall geometry.

FIG. 8C shows a more detailed implementation 890 of the essential convex X-ray source of FIG. 8B. Here curvilinear mapped components that correspond to those in FIG. 8A are parenthetically used.

FIG. 8D shows a higher output power implementation 895 of the programmable X-ray generator of FIG. 8C. In FIG. 8D, for each electron beamlet, a plate 896 of up to 10 apertures is used. Correspondingly, the target for generating X-ray is a truncated conical shape 897. In this case, the flux of each X-ray "pencil" beam can be increased with the number of electron beamlets hitting the target.

Remote Detection and Scanning

Figure 9:
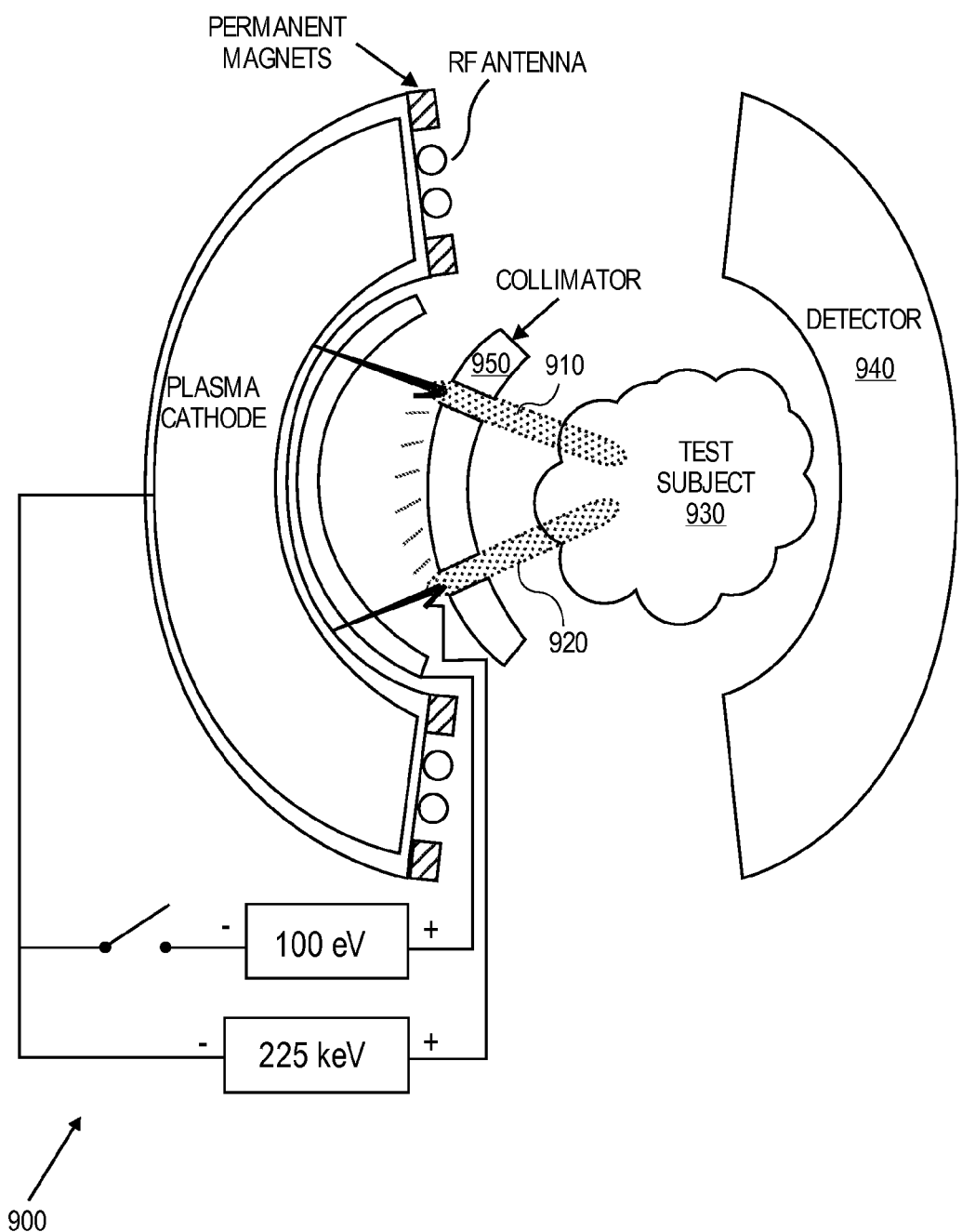
FIG. 9 is a schematic of a convex embodiment of a cylindrical section of a high flux, coded beam or beamlet X-ray source with cylindrically disposed truncated cone X-ray targets and collimators periodically illuminating a subject target disposed in front of a detector so as to allow computed tomography. Computed axial tomography of a subject disposed between the source and the detector. Compton backscatter detection and analysis of low Z elements in the subject target may be performed to detect, inter alia, explosives.

FIG. 9 shows a concave programmable X-ray source 900. Here, for example, an upper 910 and lower 920 beam of X-rays illuminate a test subject 930 for transmission X-ray analysis. The transmitted X-rays impinge upon a detector 940. By suitable illumination with source X-rays and detection by the detector 940, computed axial tomographs (CAT) may be computed by an external computer analysis system (not shown) to generate CAT scans.

The same configuration also applies to neutron generators. By simply changing the plasma from argon to deuterium and the beam extraction polarity, D-D reaction will take place at the target. The system could be very useful for neutron beam scattering imaging.

By suitably scaling the concave programmable X-ray source 900, it is believed that test subjects 930 may be placed within a space between collimator 950 and collimator 950 as much as 15 m distance. This allows for drive through scanning, container scanning for container ships and loading docks, etc. Compton backscatter may then be used to detect specific low Z elements present in a test subject, thereby potentially indicating the presence of explosives or other compounds of interest.

CONCLUSION

All publications, patents, and patent applications mentioned in this specification are herein incorporated by reference to the same extent as if each individual publication or patent application were each specifically and individually indicated to be incorporated by reference.

The description given here, and best modes of operation of the invention, are not intended to limit the scope of the invention. Many modifications, alternative constructions, and equivalents may be employed without departing from the scope and spirit of the invention.

1.1 References

[1] "Existing and Potential Standoff Explosives Detection Techniques", Committee on the Review of Existing and Potential Standoff Explosives Detection Techniques, National Research Council, 2004.

The invention claimed is:

1. A method of patterned beamlet extraction, comprising:
   a) supplying a multicusp plasma source substantially containing a plasma;
   b) providing an extractor electrode abutting the plasma,
      i) the extractor electrode comprising:
         (1) a plurality of apertures that pass through a conductive plasma side in direct contact with the plasma,
         (2) through a bulk insulator, and
         (3) continuing through a conductive exit side, wherein at least one of the extractor electrode apertures are electrically connected with the conductive exit side as the aperture gasses through the bulk insulator;
      ii) the extractor electrode comprising one side of the multicusp plasma source; and
   c) controllably biasing the conductive exit side of one or more of the apertures in the extractor electrode to extract a pattern of beamlets.

2. The method of patterned beamlet extraction of claim 1, wherein the contrallably biasing step in the extractor electrode is relative to the conductive plasma side.

3. The method of patterned beamlet extraction of claim 1, wherein the beamlets are positive ion beamlets.

4. The method of patterned beamlet extraction of claim 1, wherein the beamlets are electron beamlets.

5. The method of patterned beamlet extraction of claim 4, further comprising:
   a) providing a biased electron beamlet target sufficiently biased for X-ray production at a certain energy;
   b) impinging the electron beamlet onto the biased target, thereby producing X-rays; and
   e) collimating the X-rays to form a collimated X-ray output.

6. The method of patterned beamlet extraction of claim 4, further comprising:
   a) providing a biased electron beamlet target sufficiently biased for X-ray production at a certain energy.

7. The method of patterned beamlet extraction of claim 1, wherein the controllably biasing step comprises:
 a) biasing the exit side of the extractor electrode so as to electrostatically pull the beamlet from the multicusp plasma source.

8. The method of patterned beamlet extraction of claim 7, wherein the biasing the exit side step comprises:
 a) applying to the exit side a relative voltage of greater than 10 volts higher than the plasma side to stop extraction of an ion beam from the extractor.

9. The method of patterned beamlet extraction of claim 7, wherein the biasing the exit side step comprises:
 a) applying to the exit side a relative voltage of more than −5 volts lower than the plasma side to extract an electron beam from the extractor.

10. The method of patterned beamlet extraction of claim 1, comprising:
 a) directing the beamlets to a target substrate.

11. The method of patterned beamlet extraction of claim 10, comprising:
 a) processing the target substrate with standard photolithographic techniques to allow for maskless photolithography.

12. The method of patterned beamlet extraction of claim 10, comprising:
 a) biasing the target substrate relative to the plasma to allow for maskless ion implantation.

13. A device for patterned beamlet extraction comprising:
 a) a multicusp ion source for forming a plasma;
 b) an extractor electrode comprising one side of the multicusp ion source, said extractor electrode including a plurality of apertures that pass through from the conductive plasma side of the ion source through a bulk insulator, and continuing through a conductive exit side, wherein at least one of the extractor electrode apertures are electrically connected with the conductive exit side as the aperture passes through the bulk insulator; and,
 c) means for controllably biasing the conductive exit side of one or more of the apertures in the extractor electrode to extract a pattern of beamlets.

14. A device for patterned beamlet extraction comprising:
 a) a multicusp ion source having a plasma;
 b) computer controlled means whereby selectable patterns of electron beamlets are extracted from the plasma;
 c) a target biased relative to the plasma to impinge at least one of the electron beamlets to produce X-rays; and,
 d) a collimator proximally located to the target, whereby collimated patterned X-rays are produced.

15. The device for patterned beamlet extraction of claim 14, comprising:
 a) a substrate positioned to be exposed by the collimated patterned X-rays, which is thereby exposed without a mask.

16. A device for remote scanning, comprising:
 a) a multicusp ion source having a plasma;
 b) computer controlled means whereby selectable patterns of collimated X-rays are produced from electron beamlets extracted from the plasma;
 c) a detector disposed to detect X-ray transmission and scatter from the selectable patterns of collimated X-rays as the X-rays pass through a test subject; and
 d) a computer to analyze data input from the detector so as to provide a computed axial tomograph (CAT) scan.

17. The device for remote scanning of claim 16, comprising:
 a) a detector disposed to detect test subject generated Compton X-ray backscatter from the selectable patterns of collimated X-rays from the test subject;
 b) a computer to analyze data input from the detector so as to provide a presence of a specific chemical species present in the test subject.

18. A method of patterned beamlet extraction for the production of X-rays, comprising:
 a) supplying a multicusp plasma source substantially containing a plasma;
 b) providing an extractor electrode abutting the plasma,
  i) the extractor electrode comprising:
   (1) a plurality of apertures that pass through a conductive plasma side in direct contact with the plasma,
   (2) through a bulk insulator, and,
   (3) continuing through a conductive exit side, wherein at least one of the extractor electrode apertures are electrically connected with the conductive exit side as the aperture passes through the bulk insulator;
  ii) the extractor electrode comprising one side of the multicusp plasma source; and
 c) controllably biasing the conductive exit side of one or more of the apertures in the extractor electrode to extract a pattern of electron beamlets;
 d) providing a biased electron beamlet target sufficiently biased for X-ray production at a certain energy; and,
 e) impinging the electron beamlet onto the biased target, thereby producing X-rays.

19. The method of patterned beamlet extraction of claim 18, further comprising:
collimating the X-rays to form a collimated X-ray output.

* * * * *